(12) United States Patent
Chang et al.

(10) Patent No.: US 6,429,305 B1
(45) Date of Patent: Aug. 6, 2002

(54) FISH GROWTH HORMONES

(75) Inventors: Chi-Yao Chang, Taipei; Chia-Ching Chang, Hsinchu; Kuen-Lin Leu, Tai-Bao; Chih-Tung Tsai, Hsin-juang; Jing-Wen Ting, Taipei; Chih-Hung Lin, Tainan, all of (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/549,831

(22) Filed: Apr. 14, 2000

(51) Int. Cl.$^7$ .......................... C07H 21/04; C12P 19/34
(52) U.S. Cl. ................ 536/23.51; 536/24.3; 536/24.31; 435/91.2
(58) Field of Search .............................. 435/91.2, 320.1, 435/325, 455, 69.1, 69.4; 536/23.1, 23.51, 23.5, 24.3, 24.31

(56) References Cited

PUBLICATIONS

Kennell; Principles and Practices of Nucleic Acid Hybridization, 1971, Progr. Nucl. Acid Res. Mol. Biol.. vol. 11: 259–301.*

Ho et. al.; Cloning of the Grass Carp Growth Hormone cDNA, 1989, Biochemical and Biophysical Communications, vol. 161,No. 3: 1239–1243.*

* cited by examiner

*Primary Examiner*—Dave T. Nguyen
*Assistant Examiner*—Quang Nguyen
(74) *Attorney, Agent, or Firm*—Fish & Richardson P.C.

(57) ABSTRACT

The invention relates to new fish growth hormones, nucleic acids encoding them, and transgenic fish that express them.

2 Claims, No Drawings

SEQUENCE LISTING

<160> NUMBER OF SEQ ID NOS: 18

<210> SEQ ID NO 1
<211> LENGTH: 1410
<212> TYPE: DNA
<213> ORGANISM: Plecoglossus altivelis
<220> FEATURE:
<221> NAME/KEY: CDS
<222> LOCATION: (69)...(692)

```
<400> SEQUENCE: 1
ggcacgagca gagaccagcg attcacccag agttctctac tgacgacatc agatacgaca      60 aggacaga atg ggg caa gtg ctt ctc ctg gtg acc ctc ctg ctg gtc agt      110
        Met Gly Gln Val Leu Leu Leu Val Thr Leu Leu Leu Val Ser
          1               5                  10 gac ctg gtc aga tct gca tcc ggc tca gag aac cag cgt ctc ttc agc      158
Asp Leu Val Arg Ser Ala Ser Gly Ser Glu Asn Gln Arg Leu Phe Ser
 15                  20                  25                  30 atc gct gtc aat cgt gct caa cac ctg cac ctg ctg gcc cag aag atg      206
Ile Ala Val Asn Arg Ala Gln His Leu His Leu Leu Ala Gln Lys Met
                 35                  40                  45 ttc aac gac ttt gag gga aac ctc tct cca gat gat cga agg cag atg      254
Phe Asn Asp Phe Glu Gly Asn Leu Ser Pro Asp Asp Arg Arg Gln Met
             50                  55                  60 aat aag atc ttc ctg cag gac ttc tgt aac tca gac tcc atc atc agc      302
Asn Lys Ile Phe Leu Gln Asp Phe Cys Asn Ser Asp Ser Ile Ile Ser
         65                  70                  75 ccc gtg gac aag cac gag act cag aag agc tcg gtg cag aag ttg ctc      350
Pro Val Asp Lys His Glu Thr Gln Lys Ser Ser Val Gln Lys Leu Leu
     80                  85                  90 cac atc tcg ttc cgt ctg gtg gag tcg tgg gag tac ccc agc caa gct      398
His Ile Ser Phe Arg Leu Val Glu Ser Trp Glu Tyr Pro Ser Gln Ala
 95                 100                 105                 110 ctc agc agc tca ctg agc ctc agt cgc ttc agt gag atc cct ctg aaa      446
Leu Ser Ser Ser Leu Ser Leu Ser Arg Phe Ser Glu Ile Pro Leu Lys
                115                 120                 125 ctc acc gac ctg aag ctg ggc atc gac acc atc ctc agg ggt acc caa      494
Leu Thr Asp Leu Lys Leu Gly Ile Asp Thr Ile Leu Arg Gly Thr Gln
            130                 135                 140 gat ggg ctc ctc agc ctg gag gat aat gag gcc cag cag ctg ccc ccc      542
Asp Gly Leu Leu Ser Leu Glu Asp Asn Glu Ala Gln Gln Leu Pro Pro
        145                 150                 155 tat gag aat tac tac cag aac ctc ggg ggt gac gac aac atc cac agg      590
Tyr Glu Asn Tyr Tyr Gln Asn Leu Gly Gly Asp Asp Asn Ile His Arg
    160                 165                 170 agc tac gag ctg cta gcc tgc ttc aag aaa gac atg cac aag gtg gaa      638
Ser Tyr Glu Leu Leu Ala Cys Phe Lys Lys Asp Met His Lys Val Glu
175                 180                 185                 190 acg tac ctg act gtt gca aag tgt cgt cga tcc ctg gaa gcc aac tgt      686
Thr Tyr Leu Thr Val Ala Lys Cys Arg Arg Ser Leu Glu Ala Asn Cys
                195                 200                 205 acc ctg tagaaccacg cctgacagac agaaccaatc tatctcagat caacttagcc      742
Thr Leu ctggactgtg tcacatttaa tatcctcccc cctccatatt ccatactttc tgctttggaa      802
tgaaactata taaataaacc aacgtgtatt tacaaaaagt ataactatat attttgttaa      862
ggttcgtttg aaagcagaag gaatggaatc tctcaagacg acagagaggg aaggatgtcg      922
caatccaacg ttgttttgtt ttgaagtgta ggtttgttct gagacaccag gctcatggtt      982
ttccatctta ccaacaacag cactttctat acgtctgtct cttttcctat tagcagagtc     1042
tgattaagga tatttcagcc agataagtgt ttctaatgga ggtgaattag tttgttactc     1102
gcaaacgatt caagatacaa ttcatattgg tgctcatttt cattagaaat caaaacatac     1162
taactcacag aagatgtatg ttttaataac agtttatgtc catttgggca cattgataat     1222
gattgcctgt cgatgaaaag actcccatat gtatttgtgt tttgttttt aagtattaag      1282 agatgttttg tcatgaagac atctttctac ttgattcatt tgcctctcct ttttacttta     1342
```

```
cgtgaaatgt gtcattgttt ttaatttcta ataaagctgt tgtttattgc aaaaaaaaaa      1402
aaaaaaaa                                                                1410
```

<210> SEQ ID NO 2
<211> LENGTH: 208
<212> TYPE: PRT
<213> ORGANISM: Plecoglossus altivelis

<400> SEQUENCE: 2

```
Met Gly Gln Val Leu Leu Val Thr Leu Leu Val Ser Asp Leu
  1               5                  10                  15

Val Arg Ser Ala Ser Gly Ser Glu Asn Gln Arg Leu Phe Ser Ile Ala
             20                  25                  30

Val Asn Arg Ala Gln His Leu His Leu Leu Ala Gln Lys Met Phe Asn
         35                  40                  45

Asp Phe Glu Gly Asn Leu Ser Pro Asp Asp Arg Arg Gln Met Asn Lys
     50                  55                  60

Ile Phe Leu Gln Asp Phe Cys Asn Ser Asp Ser Ile Ile Ser Pro Val
 65                  70                  75                  80

Asp Lys His Glu Thr Gln Lys Ser Ser Val Gln Lys Leu Leu His Ile
                 85                  90                  95

Ser Phe Arg Leu Val Glu Ser Trp Glu Tyr Pro Ser Gln Ala Leu Ser
            100                 105                 110

Ser Ser Leu Ser Leu Ser Arg Phe Ser Glu Ile Pro Leu Lys Leu Thr
        115                 120                 125

Asp Leu Lys Leu Gly Ile Asp Thr Ile Leu Arg Gly Thr Gln Asp Gly
    130                 135                 140

Leu Leu Ser Leu Glu Asp Asn Glu Ala Gln Gln Leu Pro Pro Tyr Glu
145                 150                 155                 160

Asn Tyr Tyr Gln Asn Leu Gly Gly Asp Asp Asn Ile His Arg Ser Tyr
                165                 170                 175

Glu Leu Leu Ala Cys Phe Lys Lys Asp Met His Lys Val Glu Thr Tyr
            180                 185                 190

Leu Thr Val Ala Lys Cys Arg Arg Ser Leu Glu Ala Asn Cys Thr Leu
        195                 200                 205
```

<210> SEQ ID NO 3
<211> LENGTH: 22
<212> TYPE: PRT
<213> ORGANISM: Plecoglossus altivelis

<400> SEQUENCE: 3

```
Met Gly Gln Val Leu Leu Val Thr Leu Leu Val Ser Asp Leu
  1               5                  10                  15

Val Arg Ser Ala Ser Gly
             20
```

<210> SEQ ID NO 4
<211> LENGTH: 1300
<212> TYPE: DNA
<213> ORGANISM: Plecoglossus altivelis

<400> SEQUENCE: 4

```
gggcaagtgc ttctcctggt gaccctcctg ctggtcagtg acctggtcag atctgcatcc      60
ggctcagaga accagcgtct cttcagcatc gctgtcaatc gtgctcaaca cctgcacctg     120
ctggcccaga gatgttcaa cgactttgag ggaaacctct ctccagatga tcgaaggcag      180
```

```
atgaataaga tcttcctgca ggacttctgt aactcagact ccatcatcag ccccgtggac    240
aagcacgaga ctcagaagag ctcggtgcag aagttgctcc acatctcgtt ccgtctggtg    300
gagtcgtggg agtaccccag ccaagctctc agcagctcac tgagcctcag tcgcttcagt    360
gagatccctc tgaaactcac cgacctgaag ctgggcatcg acaccatcct caggggtacc    420
caagatgggc tcctcagcct ggaggataat gaggcccagc agctgccccc ctatgagaat    480
tactaccaga acctcggggg tgacgacaac atccacagga gctacgagct gctagcctgc    540
ttcaagaaag acatgcacaa ggtggaaacg tacctgactg ttgcaaagtg tcgtcgatcc    600
ctggaagcca actgtaccct gtagaaccac gcctgacaga cagaaccaat ctatctcaga    660
tcaacttagc cctggactgt gtcacattta atatcctccc ccctccatat tccatacttt    720
ctgctttgga atgaaactat ataaataaac caacgtgtat ttacaaaaag tataactata    780
tattttgtta aggttcgttt gaaagcagaa ggaatgaat ctctcaagac dacagagagg     840
gaaggatgtc gcaatccaac gttgtttgt tttgaagtgt aggtttgttc tgagacacca     900
ggctcatggt tttccatctt accaacaaca gcactttcta tacgtctgtc tcttttccta    960
ttagcagagt ctgattaagg atatttcagc cagataagtg tttctaatgg aggtgaatta    1020
gtttgttact cgcaaacgat tcaagataca attcatattg gtgctcattt tcattagaaa    1080
tcaaaacata ctaactcaca gaagatgtat gttttaataa cagtttatgt ccatttgggc    1140
acattgataa tgattgcctg tcgatgaaaa gactcccata tgtatttgtg ttttgttttt    1200
taagtattaa gagatgtttt gtcatgaaga catctttcta cttgattcat ttgcctctcc    1260
tttttacttt acgtgaaatg tgtcattgtt tttaatttct                          1300
```

<210> SEQ ID NO 5
<211> LENGTH: 972
<212> TYPE: DNA
<213> ORGANISM: Epinephlus awoara
<220> FEATURE:
<221> NAME/KEY: CDS
<222> LOCATION: (70)...(681)

<400> SEQUENCE: 5

```
acgagctcag acctgatcca ccagagccag acctgatccc ccagagccag acctaatccc    60 agaccagcc atg gac cga gtc gtc ctc ctg ctg tca gta gtg tct ctg ggc   111
           Met Asp Arg Val Val Leu Leu Leu Ser Val Val Ser Leu Gly
             1               5                  10 gtt tcc tct cag cca atc aca gac ggc cag cga ctg ttc tcc atc gct    159
Val Ser Ser Gln Pro Ile Thr Asp Gly Gln Arg Leu Phe Ser Ile Ala
 15                  20                  25                  30 gtc agc aga gtt caa cat ctc cac ctg ctt gct cag aga ctc ttc tcc    207
Val Ser Arg Val Gln His Leu His Leu Leu Ala Gln Arg Leu Phe Ser
                 35                  40                  45 gac ttt gag agc agt ctg cag aca gag gag cag cga cag ctc aac aag    255
Asp Phe Glu Ser Ser Leu Gln Thr Glu Glu Gln Arg Gln Leu Asn Lys
             50                  55                  60 atc ttc ctg cag gac ttt tgt aac tct gat tac atc atc agc ccc att    303
Ile Phe Leu Gln Asp Phe Cys Asn Ser Asp Tyr Ile Ile Ser Pro Ile
         65                  70                  75 gac aag cat gag acg cag cgc agc tcc gtg ttg aag ctg ttg tcg atc    351
Asp Lys His Glu Thr Gln Arg Ser Ser Val Leu Lys Leu Leu Ser Ile
     80                  85                  90 tcc tat cgg ttg gtg gag tcc tgg gag ttc ccc agt cgg tcc ctg tcc    399
Ser Tyr Arg Leu Val Glu Ser Trp Glu Phe Pro Ser Arg Ser Leu Ser
 95                 100                 105                 110
```

```
gga ggt tct gct ccc aga aac cag att ttt ccc aaa ctg tct gaa ttg         447
Gly Gly Ser Ala Pro Arg Asn Gln Ile Phe Pro Lys Leu Ser Glu Leu
            115                 120                 125 aaa act ggg atc ctg ctg ctg atc agg gcc aat cag gac gga gcg gag         495
Lys Thr Gly Ile Leu Leu Leu Ile Arg Ala Asn Gln Asp Gly Ala Glu
        130                 135                 140 ctc ttt cct gac agc tcc gcc ctc cag ttg gct cct tat ggg aac tat         543
Leu Phe Pro Asp Ser Ser Ala Leu Gln Leu Ala Pro Tyr Gly Asn Tyr
            145                 150                 155 tat cag agt ctg ggc gca gac gag tcg ctg cga cga acg tac gaa ctg         591
Tyr Gln Ser Leu Gly Ala Asp Glu Ser Leu Arg Arg Thr Tyr Glu Leu
    160                 165                 170 ctg gcg tgt ttc aag aaa gac atg cac aag gtg gag acc tac ctg acg         639
Leu Ala Cys Phe Lys Lys Asp Met His Lys Val Glu Thr Tyr Leu Thr
175                 180                 185                 190 gtg gct aaa tgt cga ctc tct cct gag gcc aac tgt acc ctg                 681
Val Ala Lys Cys Arg Leu Ser Pro Glu Ala Asn Cys Thr Leu
                195                 200 tagccccgcc tctccagtat gaagacaagc ccccatgtgg atgatgtaat gctgtgtgtt       741
ctgtagtccc gcccacatgt tttctgactc tgctaattag cattagtgtt agccacagtg       801
ttagcctgtg ttcagtggtt tgttggagca ggtgttatta tgatgacagc cgtcgacagg       861
aagtgatgtc attttgtcac catgtgtaat aaagtgtgtg ctgtgttgca ttcaaaaaaa       921
aaaaaaaaaa aaaaaaaaaa aaaaaaaaaa aaaaaaaaaa aaaaaaaaa a                 972

<210> SEQ ID NO 6
<211> LENGTH: 204
<212> TYPE: PRT
<213> ORGANISM: Epinephlus awoara

<400> SEQUENCE: 6

Met Asp Arg Val Val Leu Leu Ser Val Val Ser Leu Gly Val Ser
 1               5                  10                  15

Ser Gln Pro Ile Thr Asp Gly Arg Leu Phe Ser Ile Ala Val Ser
            20                  25                  30

Arg Val Gln His Leu His Leu Leu Ala Gln Arg Leu Phe Ser Asp Phe
        35                  40                  45

Glu Ser Ser Leu Gln Thr Glu Glu Gln Arg Gln Leu Asn Lys Ile Phe
    50                  55                  60

Leu Gln Asp Phe Cys Asn Ser Asp Tyr Ile Ile Ser Pro Ile Asp Lys
65                  70                  75                  80

His Glu Thr Gln Arg Ser Ser Val Leu Lys Leu Leu Ser Ile Ser Tyr
                85                  90                  95

Arg Leu Val Glu Ser Trp Glu Phe Pro Ser Arg Ser Leu Ser Gly Gly
            100                 105                 110

Ser Ala Pro Arg Asn Gln Ile Phe Pro Lys Leu Ser Glu Leu Lys Thr
        115                 120                 125

Gly Ile Leu Leu Ile Arg Ala Asn Gln Asp Gly Ala Glu Leu Phe
    130                 135                 140

Pro Asp Ser Ser Ala Leu Gln Leu Ala Pro Tyr Gly Asn Tyr Tyr Gln
145                 150                 155                 160

Ser Leu Gly Ala Asp Glu Ser Leu Arg Arg Thr Tyr Glu Leu Leu Ala
                165                 170                 175

Cys Phe Lys Lys Asp Met His Lys Val Glu Thr Tyr Leu Thr Val Ala
            180                 185                 190
```

```
Lys Cys Arg Leu Ser Pro Glu Ala Asn Cys Thr Leu
        195                 200
```

<210> SEQ ID NO 7
<211> LENGTH: 19
<212> TYPE: PRT
<213> ORGANISM: Epinephelus awoara

<400> SEQUENCE: 7

```
Met Asp Arg Val Val Leu Leu Ser Val Val Ser Leu Gly Val Ser
  1               5                  10                  15

Ser Gln Pro
```

<210> SEQ ID NO 8
<211> LENGTH: 816
<212> TYPE: DNA
<213> ORGANISM: Epinephelus awoara

<400> SEQUENCE: 8

```
gaccgagtcg tcctcctgct gtcagtagtg tctctgggcg tttcctctca gccaatcaca      60
gacggccagc gactgttctc catcgctgtc agcagagttc aacatctcca cctgcttgct     120
cagagactct tctccgactt tgagagcagt ctgcagacag aggagcagcg acagctcaac     180
aagatcttcc tgcaggactt tgtaactct gattacatca tcagcccat tgacaagcat       240
gagacgcagc gcagctccgt gttgaagctg ttgtcgatct cctatcggtt ggtggagtcc     300
tgggagttcc ccagtcggtc cctgtccgga ggttctgctc ccagaaacca gattttccc     360
aaactgtctg aattgaaaac tgggatcctg ctgctgatca gggccaatca ggacggagcg     420
gagctctttc ctgacagctc cgccctccag ttggctcctt atgggaacta ttatcagagt     480
ctgggcgcag acgagtcgct gcgacgaacg tacgaactgc tggcgtgttt caagaaagac     540
atgcacaagg tggagaccta cctgacggtg gctaaatgtc gactctctcc tgaggccaac     600
tgtaccctgt agccccgcct ctccagtatg aagacaagcc cccatgtgga tgatgtaatg     660
ctgtgtgttc tgtagtcccg cccacatgtt ttctgactct gctaattagc attagtgtta     720
gccacagtgt tagcctgtgt tcagtggttt gttggagcag gtgttattat gatgacagcc     780
gtcgacagga agtgatgtca ttttgtcacc atgtgt                                816
```

<210> SEQ ID NO 9
<211> LENGTH: 1195
<212> TYPE: DNA
<213> ORGANISM: Danio rerio
<220> FEATURE:
<221> NAME/KEY: CDS
<222> LOCATION: (38)...(667)

<400> SEQUENCE: 9

```
ccttcaatca agaacgagtt tgtctatctt ggacaaa atg gct aga gca ttg gtg       55
                                        Met Ala Arg Ala Leu Val
                                          1               5 ctg ttg cag ttg gtg gtg gtt agt ttg ctg gtg aat cag ggg aaa gcc      103
Leu Leu Gln Leu Val Val Val Ser Leu Leu Val Asn Gln Gly Lys Ala
         10                  15                  20 tcc gaa aac cag cgg ctc ttc aac aac gca gtc atc cgt gtg caa cac      151
Ser Glu Asn Gln Arg Leu Phe Asn Asn Ala Val Ile Arg Val Gln His
     25                  30                  35 ctt cac cag ctg gct gca aaa atg att aac gac ttt gag gaa ggt ctt      199
Leu His Gln Leu Ala Ala Lys Met Ile Asn Asp Phe Glu Glu Gly Leu
 40                  45                  50
```

-continued

| | | |
|---|---|---|
| atg cct gag gaa cgc aga cag ttg agt aaa atc ttc cct ctg tcg ttc<br>Met Pro Glu Glu Arg Arg Gln Leu Ser Lys Ile Phe Pro Leu Ser Phe<br>55                         60                        65                        70 | 247 |
| tgc aac tct gac tcc atc gag acg ccg acg gga aaa gat gaa acg caa<br>Cys Asn Ser Asp Ser Ile Glu Thr Pro Thr Gly Lys Asp Glu Thr Gln<br>75                         80                        85 | 295 |
| aaa agc tct atg ttg aag ctg ctt cgt atc tct ttc cgc ctc att gaa<br>Lys Ser Ser Met Leu Lys Leu Leu Arg Ile Ser Phe Arg Leu Ile Glu<br>90                         95                       100 | 343 |
| tcc tgg gag ttt ccc agc cag acc ttg agc tcc act atc tca aac agc<br>Ser Trp Glu Phe Pro Ser Gln Thr Leu Ser Ser Thr Ile Ser Asn Ser<br>105                        110                    115 | 391 |
| ctg acc atc gga aac ccc aac caa atc act gag aaa ctg gcg gac ctg<br>Leu Thr Ile Gly Asn Pro Asn Gln Ile Thr Glu Lys Leu Ala Asp Leu<br>120                       125                    130 | 439 |
| aaa atg ggc atc agc gtg ctc atc aag gga tgt ctc gat gga cag cca<br>Lys Met Gly Ile Ser Val Leu Ile Lys Gly Cys Leu Asp Gly Gln Pro<br>135                140                  145                  150 | 487 |
| aat atg gat gac aac gac tcc ctg ccg ttg cct ttt gag gat ttc tac<br>Asn Met Asp Asp Asn Asp Ser Leu Pro Leu Pro Phe Glu Asp Phe Tyr<br>155                       160                    165 | 535 |
| ctg acc gta ggg gag acc agt ctc aga gag agc ttt cgc ctg ctg gcc<br>Leu Thr Val Gly Glu Thr Ser Leu Arg Glu Ser Phe Arg Leu Leu Ala<br>170                       175                    180 | 583 |
| tgc ttc aag aag gac atg cac aag gtg gaa act tac ctg agg gtt gcg<br>Cys Phe Lys Lys Asp Met His Lys Val Glu Thr Tyr Leu Arg Val Ala<br>185                       190                    195 | 631 |
| aat tgc agg aga tct ctg gat tcc aac tgt acc ctg tagagggcgc<br>Asn Cys Arg Arg Ser Leu Asp Ser Asn Cys Thr Leu<br>200                     205                    210 | 677 |
| taatgtattg ctagtcaaag cctgctttat cctttctgc aaatctaaga ccagtttgca | 737 |
| ttatcaaaac ataaactaat tattatctgg tcctatatat gcaggaaata tcaagcaggc | 797 |
| atggctggat ctgtacttta tttcccttcc ataaacctta cacctaccac cattgtattt | 857 |
| attcttctta ttgggaagta ttatcatttc aagatgttcc ttaaaaacgt aaatattgat | 917 |
| tcttatttaa tatccgaacc ttattcacag tggtgcttag caatttctgg cgatattttc | 977 |
| ttaaatgtgc caaaattgac ttaaatcaaa gtgctaatat tgtgctttgg tgtatattat | 1037 |
| atctaaaaca gttaaagatc agtgttcaaa gggttcactc ccaaatgtgt gaatggaaac | 1097 |
| gtgtctgtct gatagattct tgccttaata ttatcaactc atcctgttct attctaactg | 1157 |
| tatcaattaa agttttaaaa tgcaaaaaaa aaaaaaaa | 1195 |

<210> SEQ ID NO 10
<211> LENGTH: 210
<212> TYPE: PRT
<213> ORGANISM: Danio rerio

<400> SEQUENCE: 10

Met Ala Arg Ala Leu Val Leu Leu Gln Leu Val Val Ser Leu Leu
1                  5                        10                        15

Val Asn Gln Gly Lys Ala Ser Glu Asn Gln Arg Leu Phe Asn Asn Ala
                   20                        25                        30

Val Ile Arg Val Gln His Leu His Gln Leu Ala Ala Lys Met Ile Asn
                   35                        40                        45

Asp Phe Glu Glu Gly Leu Met Pro Glu Glu Arg Arg Gln Leu Ser Lys
     50                        55                        60

Ile Phe Pro Leu Ser Phe Cys Asn Ser Asp Ser Ile Glu Thr Pro Thr

```
                        65                  70                  75                  80
Gly Lys Asp Glu Thr Gln Lys Ser Ser Met Leu Lys Leu Leu Arg Ile
                        85                  90                  95

Ser Phe Arg Leu Ile Glu Ser Trp Glu Phe Pro Ser Gln Thr Leu Ser
                100                 105                 110

Ser Thr Ile Ser Asn Ser Leu Thr Ile Gly Asn Pro Asn Gln Ile Thr
            115                 120                 125

Glu Lys Leu Ala Asp Leu Lys Met Gly Ile Ser Val Leu Ile Lys Gly
        130                 135                 140

Cys Leu Asp Gly Gln Pro Asn Met Asp Asp Asn Asp Ser Leu Pro Leu
145                 150                 155                 160

Pro Phe Glu Asp Phe Tyr Leu Thr Val Gly Glu Thr Ser Leu Arg Glu
                165                 170                 175

Ser Phe Arg Leu Leu Ala Cys Phe Lys Lys Asp Met His Lys Val Glu
                180                 185                 190

Thr Tyr Leu Arg Val Ala Asn Cys Arg Arg Ser Leu Asp Ser Asn Cys
            195                 200                 205

Thr Leu
    210

<210> SEQ ID NO 11
<211> LENGTH: 22
<212> TYPE: PRT
<213> ORGANISM: Danio rerio

<400> SEQUENCE: 11

Met Ala Arg Ala Leu Val Leu Leu Gln Leu Val Val Val Ser Leu Leu
  1               5                  10                  15

Val Asn Gln Gly Lys Ala
            20

<210> SEQ ID NO 12
<211> LENGTH: 1083
<212> TYPE: DNA
<213> ORGANISM: Danio rerio

<400> SEQUENCE: 12
gctagagcat tggtgctgtt gcagttggtg gtggttagtt tgctggtgaa tcaggggaaa      60
gcctccgaaa accagcggct cttcaacaac gcagtcatcc gtgtgcaaca ccttcaccag     120
ctggctgcaa aaatgattaa cgactttgag gaaggtctta tgcctgagga acgcagacag     180
ttgagtaaaa tcttccctct gtcgttctgc aactctgact ccatcgagac gccgacggga     240
aaagatgaaa cgcaaaaaag ctctatgttg aagctgcttc gtatctcttt ccgcctcatt     300
gaatcctggg agtttcccag ccagaccttg agctccacta tctcaaacag cctgaccatc     360
ggaaacccca accaaatcac tgagaaactg gcggacctga aaatgggcat cagcgtgctc     420
atcaagggat gtctcgatgg acagccaaat atggatgaca cgactccct gccgttgcct      480 tttgaggatt tctacctgac cgtaggggag accagtctca gagagagctt cgcctgctg      540 gcctgcttca agaaggacat gcacaaggtg gaaacttacc tgagggttgc gaattgcagg     600
agatctctgg attccaactg taccctgtag agggcgctaa tgtattgcta gtcaaagcct     660
gctttatcct tttctgcaaa tctaagacca gtttgcatta tcaaaacata aactaattat     720
tatctggtcc tatatatgca ggaaatatca agcaggcatg gctggatctg tacttatt      780 ccctcccata aaccttacac ctaccaccat tgtatttatt cttcttattg ggaagtatta     840
```

```
tcatttcaag atgttcctta aaaacgtaaa tattgattct tatttaatat ccgaaccttta    900 ttcacagtgg tgcttagcaa tttctggcga tattttctta aatgtgccaa aattgactta    960
aatcaaagtg ctaatattgt gctttggtgt atattatatc taaaacagtt aaagatcagt   1020
gttcaaaggg ttcactccca aatgtgtgaa tggaaacgtg tctgtctgat agattcttgc   1080
ctt                                                                 1083

<210> SEQ ID NO 13
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 13
caamayctbc accwrytsgc ysmr                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 14
cttgtgcatg tcyttyttra arca                                            24

<210> SEQ ID NO 15
<211> LENGTH: 8
<212> TYPE: PRT
<213> ORGANISM: Artificial Sequence
<220> FEATURE:
<223> OTHER INFORMATION: Synthetically derived peptide

<400> SEQUENCE: 15

Leu Glu His His His His His His
 1               5

<210> SEQ ID NO 16
<211> LENGTH: 29
<212> TYPE: DNA
<213> ORGANISM: Artificial Sequence
<220> FEATURE:
<223> OTHER INFORMATION: Synthetically derived primer

<400> SEQUENCE: 16
aattccatat gtcagagaac cagcgtgta                                       29

<210> SEQ ID NO 17
<211> LENGTH: 27
<212> TYPE: DNA
<213> ORGANISM: Artificial Sequence
<220> FEATURE:
<223> OTHER INFORMATION: Synthetically derived primer

<400> SEQUENCE: 17
ccgctcgagc agggtacagt tggcttc                                         27

<210> SEQ ID NO 18
<211> LENGTH: 32
<212> TYPE: DNA
```

```
-continued

<213> ORGANISM: Artificial Sequence
<220> FEATURE:
<223> OTHER INFORMATION: Synthetically derived primer

<400> SEQUENCE: 18
aattccatat gatcacagac ggccagcgac tg                                    32
```

FISH GROWTH HORMONES

BACKGROUND OF THE INVENTION

Farmed fish, such as ayu or grouper, are commercially valuable crops. A means of increasing the growth rate or size of fish crops is therefore commercially useful.

SUMMARY OF THE INVENTION

The invention is based on the discovery of three new fish growth hormone genes (from Plecoglossus altivelis, Epinephelus awoara, and Danio rerio) that can be used to increase fish crop production. For example, each of the new fish growth hormone genes can be used to generate transgenic fish expressing a fish growth hormone of the invention. These fish will exhibit greater growth rates and body sizes than the parent fish from which the transgenic fish was derived. Alternatively, the growth hormones can be recombinantly produced and introduced into the fish diet (see, e.g., Ben-Atia et al., Gen. Compar. Endocrinol. 113:155–164, 1999).

In addition, the growth hormone polypeptides and fragments thereof can be used to generate antibodies that specifically bind to a growth hormone of the invention. These antibodies can be used to, e.g., detect fish pituitary tissue in a sample. Other fragments, such as the signal sequence, can be fused to heterologous proteins to render them secretable. The growth hormone cDNA and fragments thereof can be used to screen DNA libraries (e.g., genomic or cDNA libraries) to isolate other related genes and the growth hormones which they encode.

The sequences of the new fish growth hormones are given below:

```
Plecoglossus altivelis (common name: ayu)

GGCACGAGCA GAGACCAGCG ATTCACCCAG AGTTCTCTAC TGACGACATC AGATACGACA

AGGACAGAAT GGGGCAAGTG CTTCTCCTGG TGACCCTCCT GCTGGTCAGT GACCTGGTCA
            M   G   Q   V   L   L   L   V   T   L   L   L   V   S   D   L   V

GATCTGCATC CGGCTCAGAG AACCAGCGTC TCTTCAGCAT CGCTGTCAAT CGTGCTCAAC
 R   S   A   S   G   S   E   N   Q   R   L   F   S   I   A   V   N   R   A   Q

ACCTGCACCT GCTGGCCCAG AAGATGTTCA ACGACTTTGA GGGAAACCTC TCTCCAGATG
 H   L   H   L   L   A   Q   K   M   F   N   D   F   E   G   N   L   S   P   D

ATCGAAGGCA GATGAATAAG ATCTTCCTGC AGGACTTCTG TAACTCAGAC TCCATCATCA
 D   R   R   Q   M   N   K   I   F   L   Q   D   F   C   N   S   D   S   I   I

GCCCCGTGGA CAAGCACGAG ACTCAGAAGA GCTCGGTGCA GAAGTTGCTC CACATCTCGT
 S   P   V   D   K   H   E   T   Q   K   S   S   V   Q   K   L   L   H   I   S

TCCGTCTGGT GGAGTCGTGG GAGTACCCCA GCCAACCTCT CAGCACCTCA CTGACCCTCA
 F   R   L   V   E   S   W   E   Y   P   S   Q   A   L   S   S   S   L   S   L

GTCGCTTCAG TGAGATCCCT CTGAAACTCA CCGACCTGAA GCTGGGCATC GACACCATCC
 S   R   F   S   E   I   P   L   K   L   T   D   L   K   L   G   I   D   T   I

TCAGGGGTAC CCAAGATGGG CTCCTCAGCC TGGAGGATAA TGAGGCCCAG CAGCTGCCCC
 L   R   G   T   Q   D   G   L   L   S   L   E   D   N   E   A   Q   Q   L   P

CCTATGAGAA TTACTACCAG AACCTCGGGG GTGACGACAA CATCCACAGG AGCTACGAGC
 P   Y   E   N   Y   Y   Q   N   L   G   G   D   D   N   I   H   R   S   Y   E

TGCTAGCCTG CTTCAAGAAA GACATGCACA AGGTGGAAAC GTACCTGACT GTTGCAAAGT
 L   L   A   C   F   K   K   D   M   H   K   V   E   T   Y   L   T   V   A   K

GTCGTCGATC CCTCGAAGCC AACTGTACCC TGTAGAACCA CGCCTGACAG ACAGAACCAA
 C   R   R   S   L   E   A   N   C   T   L   *  (SEQ ID NO:2)

TCTATCTCAG ATCAACTTAG CCCTGGACTG TGTCACATTT AATATCCTCC CCCCTCCATA

TTCCATACTT TCTGCTTTGG AATGAAACTA TATAAATAAA CCAACGTGTA TTTACAAAAA

GTATAACTAT ATATTTTGTT AAGGTTCGTT TGPAAGCAGA AGGAATGGAA TCTCTCAAGA

GGACAGAGAG GGAAGGATGT CGCAATCCAA CGTTGTTTTG TTTTGAAGTG TAGGTTTGTT

CTGAGACACC AGGCTCATGG TTTTCCATCT TACCAACAAC AGCACTTTCT ATACGTCTGT

GTCTTTTCCT ATTAGGAGAG TCTGATTAAG GATATTTCAG CCAGATAAGT GTTTCTAATG

GAGGTGAATT AGTTTGTTAC TCGCAAACGA TTCAAGATAC AATTCATATT GGTGCTCATT
```

-continued

TTCATTAGAA ATCAAAACAT ACTAACTCAC AGAAGATGTA TGTTTTAATA ACAGTTTATG

TCCATTTGGG CACATTGATA ATGATTGCCT GTCGATGAAA AGACTCCCAT ATGTATTTGT

GTTTTGTTTT TTAAGTATTA AGAGATGTTT TGTCATGAAG ACATCTTTCT ACTTGATTCA

TTTGCCTCTC CTTTTTACTT TACGTGAAAT GTGTCATTGT TTTTAATTTC TAATAAAGCT

GTTGTTTATT GCAAAAAAAA AAAAAAAAAA (SEQ ID NO:1)

The leader peptide sequence (SEQ ID NO:3) is shown in bold, and the polyA signal is underlined. The nucleotide sequence between the initiation codon and the polyA signal, excluding the initiation codon and the polyA signal, is designated SEQ ID NO:4.

Epinephelus awoara (common name: yellow grouper)

```
ACGAGCTCAG ACCTGATCCA CCAGAGCCAG ACCTGATCCC CCAGAGCCAG ACCTAATCCC

AGACCAGCCA TGGACCGAGT CGTCCTCCTG CTGTCAGTAG TGTCTCTGGG CGTTTCCTCT
            M   D   R   V   V   L   L   L   S   V   V   S   L   G   V   G   S

CAGCCAATCA CAGACGGCCA GCGACTGTTC TCCATCGCTG TCAGCAGAGT TCAACATCTC
 Q P   I T   D G   Q R L F   S I A   V S R V   Q R L

CACCTGCTTG CTCAGAGACT CTTCTCCGAC TTTGAGAGCA GTCTGCAGAC AGAGGAGCAG
 H L   L A   Q R   L F S D   F E   S   S L Q T   E E Q

CGACAGCTCA ACAAGATCTT CCTGCAGGAC TTTTGTAACT CTGATTACAT CATCAGCCCC
 R Q   L N   K I   F L Q D   F C   N   S D Y I   I S P

ATTGACAAGC ATGAGACGCA GCGCAGCTCC GTGTTGAAGC TGTTGTCGAT CTCCTATCGG
 I D K H   E T   Q R S S   V L K   L L S I   S Y R

TTGGTGGAGT CCTGGGAGTT CCCCAGTCGG TCCCTGTCCG GAGGTTCTGC TCCCAGAAAC
 L V   E S   W E   F P S R   S L   S   G G S A   P R N

CAGATTTTTC CCAAACTGTC TGAATTGAAA ACTGGGATCC TGCTGCTGAT CAGGGCCAAT
 Q I   F P   K L   S E L K   T G   I   L L L I   R A N

CAGGACGGAG CGGAGCTCTT TCCTGACAGC TCCGCCCTCC AGTTGGCTCC TTATGGGAAC
 Q D   G A   E L   F P D S   S A   L   Q L A P   Y G N

TATTATCAGA GTCTGGGCGC AGACGAGTCG CTGCGACGAA CGTACGAACT GCTGGCGTGT
 Y Y   Q S   L G   A D E S   L R   R   T Y E L   L A C

TTCAAGAAAG ACATGCACAA GGTGGAGACC TACCTGACGG TGGCTAAATG TCGACTCTCT
 F K   K D   M H   K V E T   Y L   T   V A K C   R L S

CCTGAGGCCA ACTGTACCCT GTAGCCCCGC CTCTCCAGTA TGAAGACAAG CCCCCATGTG
 P E   A N   C T   L * (SEQ ID NO:6)

GATGATGTAA TGCTGTGTGT TCTGTAGTCC CGCCCACATG TTTTCTGACT CTGCTAATTA

GCATTAGTGT TAGCCACAGT GTTAGCCTGT GTTCAGTGGT TTGTTGGAGC AGGTGTTATT

ATGATGACAG CCGTCGACAG GAAGTGATGT CATTTGTCA CCATGTGTAATAAAGTGTGT

GCTGTGTTGC ATTCAAAAAA AAAAAAAAAA AAAAAAAAA AAAAAAAAAA AAAAAAAAAA

AAAAAAAAAA AA (SEQ ID NO.5)
```

The leader peptide sequence (SEQ ID NO:7) is shown in bold, and the polyA signal is underlined. The nucleotide sequence between the initiation codon and the polyA signal, excluding the initiation codon and the polyA signal, is designated SEQ ID NO:8.

Danio rerio (common name: zebrafish)

```
CCTTCAATCA AGAACGAGTT TGTCTATCTT GGACAAAATG GCTAGAGCAT TGGTGCTGTT
                                         M   A  R  A   L  V  L  L

GCAGTTGGTG GTGGTTAGTT TGCTGGTGAA TCAGGGAAA GCCTCCGAAA ACCAGCGGCT
 Q  L  V   V  V  S  L L   V  N  Q  G  K   A  S  D   N  Q  R  L

CTTCAACAAC GCAGTCATCC GTGTGCAACA CCTTCACCAG CTGGCTGCAA AAATGATTAA
 F  N  N   A  V  I  R V   Q  H  L  H  Q   L  A  A   K  M  I  N

CGACTTTGAG GAAGGTCTTA TGCCTGAGGA ACGCAGACAG TTGAGTAAAA TCTTCCCTCT
 D  F  E   G  L  M  P E   E  R  R  Q   L  S  K   I  F  P  L

GTCGTTCTGC AACTCTGACT CCATCGAGAC GCCGACGGGA AAAGATGAAA CGCAAAAAAG
 S  F  C   N  S  D  S I   E  T  P  T  G   K  D  E   T  Q  K  S

CTCTATGTTG AAGCTGCTTC GTATCTCTTT CCGCCTCATT GAATCCTGGG AGTTTCCCAG
 S  M  L   K  L  L  R I   S  F  R  L  I   E  S  W   E  F  P  S

CCAGACCTTG AGCTCCACTA TCTCAAACAG CCTGACCATC GGMACCCCA ACCAAATCAC
 Q  T  L   S  S  T  I S   N  S  L  T  I   G  N  P   N  Q  L  T

TGAGAAACTG GCGGACCTGA AAATGGGCAT CAGCGTGCTC ATCAAGGGAT GTCTCGATGG
 E  K  L   A  D  L  K M   G  I  S  V  L   I  K  G   C  L  D  G

ACAGCCAAAT ATGGATGACA ACGACTCCCT GCCGTTGCCT TTTGAGGATT TCTACCTGAC
 Q  P  N   M  D  D  N D   S  L  P  L  P   F  E  D   F  Y  L  T

CGTAGGGGAG ACCAGTCTCA GAGAGAGCTT TCGCCTGCTG GCCTGCTTCA AGAAGGACAT
 V  G  D   T  S  L  R E   S  F  R  L  L   A  C  F   K  K  D  M

GCACAACGTG GAAACTTACC TGAGGCTTGC GAATTGCAGG AGATCTCTGG ATTCCAACTG
 H  K  V   E  T  Y  L R   V  A  N  C  R   R  S  L   D  S  N  C

TACCCTCTAG AGGGCCCTAA TGTATTGCTA GTCAAAGCCT GCTTTATCCT TTTCTGCAAA
 T  L  *  (SEQ ID NO:10)

TCTAAGACCA GTTTGCATTA TCAAAACATA AACTAATTAT TATCTGGTCC TATATATGCA

GGAAATATCA AGCAGGCATG GCTGGATCTG TACTTTATTT CCCTTCCATA AACCTTACAC

CTACCACCAT TGTATTTATT CTTCTTATTG GGAAGTATTA TCATTTCAAG ATGTTCCTTA

AAAACGTAAA TATTGATTCT TATTTAATAT CCGAACCTTA TTCACAGTGG TGCTTAGCAA

TTTCTGGCGA TATTTTCTTA AATGTGCCAA AATTGACTTA AATCAAAGTG CTAATATTGT

GCTTTGGTGT ATATTATATC TAAAACAGTT AAAGATCAGT GTTCAAAGGG TTCACTCCCA

AATGTGTGAA TGGAAACGTG TCTGTCTGAT AGATTCTTGC CTTAATATTA TCAACTCATC

CTGTTCTATT CTAACTGTAT CAATTAAAGT TTTAAAATGC AAAAAAAAAA AAAAA (SEQ ID NO:9)
```

The leader peptide sequence (SEQ ID NO:11) is shown in bold, and the putative polyA signal is underlined. The nucleotide sequence between the initiation codon and the polyA signal, excluding the initiation codon and the polyA signal, is designated SEQ ID NO:12.

Accordingly, the invention features a substantially pure polypeptide having an amino acid sequence at least 75% (e.g., 80, 85, 90, 95, or 100%) identical to SEQ ID NO:2, at least 97% (e.g., 98, 99, or 100%) identical to SEQ ID NO:6, or at least 92% (e.g., 95, 98, or 100%) identical to SEQ ID NO: 10. The polypeptide increases cell proliferation, i.e., when a cell is contacted with the polypeptide in vivo or in vitro, the cell exhibits or will exhibit increased proliferation in comparison to a cell without contact with the polypeptide. Also featured is (1) a substantially pure polypeptide encoded by a nucleic acid that hybridizes under stringent conditions to a nucleic acid consisting of any one of SEQ ID NOs:4, 8, and 12; and (2) a substantially pure polypeptide having any one of SEQ ID NOs:2, 6, and 10 with up to 10 (e.g., 2, 4, 5, 6, or 8) conservative amino acid substitutions.

The invention includes (1) an isolated nucleic acid which hybridizes under stringent conditions to any one of SEQ ID NOs:4, 8, and 12, e.g., a nucleic acid that encodes a polypeptide that increases cell proliferation; (2) an isolated nucleic acid which hybridizes under stringent conditions to any one of SEQ ID NOs: 1, 5, and 9, where the nucleic acid is at least 20 (e.g., at least 30, 40, 50, 100, 200, and 300) nucleotides in length and does not contain 10 consecutive adenine residues; and (3) a nucleic acid encoding any polypeptide of the invention. A nucleic acid of the invention can also be less than 10,000, 1000, 500, 100, 50, or 25 thousand nucleotides in length.

In addition, the invention features a transgenic fish whose genomic DNA comprises a foreign sequence encoding a polypeptide of the invention, wherein the transgenic fish exhibits increased cell proliferation as compared to a reference fish whose genomic DNA does not have the foreign sequence. The transgenic fish can be a salmoniform (e.g., a member of the genus Plecoglossus), a perciform (e.g., a member of the genus Epinephelus), or a cypriniform (e.g., a member of the genus Danio).

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

By hybridization under "stringent conditions" is meant hybridization at 65° C., 0.5 X SSC, followed by washing at 45° C., 0.1 X SSC.

The "percent identity" of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403–410, 1990). BLAST nucleotide searches are performed with the NBLAST program, score =100, wordlength=12. BLAST protein searches are performed with the XBLAST program, score= 50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

By "cell proliferation" is meant an increase in cell number or cell size.

By "foreign sequence" as applied to a transgenic fish is meant a nucleotide sequence that does not naturally occur in the parent fish from which the transgenic fish was derived. Thus, a foreign sequence includes a non-naturally occurring additional copy of a sequence found in the parent fish or a new sequence of a fish species different from the parent fish species.

Other features or advantages of the present invention will be apparent from the following detailed description, and also from the claims.

DETAILED DESCRIPTION

The invention relates to new fish growth hormones and their use in promoting cell proliferation and isolating other related growth hormone genes. Contemplated within the scope of the invention are transgenic fish harboring a gene that expresses a polypeptide of the invention. These fish exhibit increased cell proliferation as compared to a non-transgenic parent fish. The production of transgenic fish is well known in the art and can be produced using electroporation (Inoue et al., Cell Diff. Dev. 29:123–128, 1990; Müller et al., Mol. Marine Biol. Biotech. 1:276–281, 1992; and Patil et al., J. Exp. Zoology 274:121–129, 1996), particle bombardment (Zelenin et al., FEBS 287:118–120, 1991), Baekonization (Zhao et al., Mol. Marine Biol. Biotech. 2:63–69, 1993), or the procedures in the Examples below.

Without further elaboration, it is believed that one skilled in the art can, based on the above disclosure, the isolation of growth hormone genes described below, and the production of transgenic fish described below, utilize the present invention to its fullest extent. The following examples are to be construed as merely illustrative of how one skilled in the art can isolate and use the polypeptides and nucleic acids of the invention, and are not limitative of the remainder of the disclosure in any way. Any publications cited in this disclosure are hereby incorporated by reference.

EXAMPLE

The isolation and characterization of fish growth hormone genes were carried out using the following methods.

Molecular cloning of growth hormone genes. About one hundred pituitary glands each of ayu and yellow grouper were collected. mRNA (about 5 mg) were isolated from pituitary glands using an mRNA isolation kit (Stratagene). cDNA were synthesis using a cDNA library synthesis kit (Stratagene). The inserts of interest were cloned into a ZAP expression vector (Stratagene) and packaged to produce ayu and yellow grouper pituitary cDNA libraries.

A pair of degenerated primers were designed based on the sequences of common carp, tuna, red sea bream, rainbow trout, yellow tail, and chum salmon growth hormone genes. mRNA was extracted from pituitary glands of ayu, yellow grouper, and zebrafish, and the corresponding growth hormone cDNA were amplified from the mRNA using RT-PCR and the degenerate primers. Labelled probes were then produced from these amplified fragments using a random primer synthesis kit (RediPrime II, Amersham). The probes were used to screen the ayu and yellow grouper pituitary cDNA libraries, as well as a zebrafish head cDNA library. Purified positive clones were sequenced using an ABI autosequencer model 377.

Expression of new growth hormones. For the sake of simplicity, the ayu, yellow grouper, and zebrafish recombinant growth hormones will be abbreviated rPaGH, rEaGH, and rDrGH, respectively. Growth hormone cDNA clones were PCR amplified using primers designed to contain convenient restriction sites. The amplified fragments were digested with NdeI and XhoI and cloned into similarly digested PET-20b(+) (Novagen). The resulting 15 vectors were then used to transform E. coli BL21 (DE3)pLysS.

Transformed host cells growing to an $OD_{600}$ of 0.3 were induced with 0.1 mM isopropyl β-D-thiogalactopyranoside (IPTG) and then incubated at 37° C. for 16 hours. The induced proteins were isolated and examined using SDS-PAGE. The SDS-PAGE bands were then excised from the gel and sequenced using an ABI model 477 protein sequencer to ensure that the recombinantly produced proteins were authentic.

Recombinant protein isolation. Inclusion bodies were isolated from transformed bacteria generally using the methods described in Giza et al., Gene 78:73–84, 1989. Induced bacteria were harvested by centrifugation at 4000×g for 30 minutes. The cell pellet was then suspended in and mixed well with ice cold lysis buffer 1 (50 mM Tris [pH 7.8], 200 mM NaCl, 0.1 mM EDTA, 5% glycerol). To the mixture was then added 1/10 volume cell lysis buffer 2 (50 mM EDTA, 10% Triton X-100). Finally, lysozyme was added to a final concentration 10 μg/ml to facilitate cell wall breakage. The reaction mixture was put on ice for 3 hours. To facilitate cell wall breakage, the mixture was sonicated immediately after the incubation. DNA was digested with DNase I at 37° C. for 1 hour. Steps were repeated as necessary to ensure complete lysis of the host cells.

Total cell lysate was separated into soluble and insoluble portions by centrifugation at 4000×g for 30 minutes. The insoluble pellet (protein) was collected and washed twice with ice cold, double distilled water. The precipitated protein was denatured and renatured as described in Giza et al., Gene 78:73–84, 1989. The pellet was dissolved in 30 ml of 4.5 M urea, 10 mM Tris-HCI, and 0.1M β-mercaptoethanol. The pH of the mixture was raised to about 11–13 by adding NaOH as needed, to dissolve the pellet.

Quantitation and secondary structure determination of recombinant growth hormones. For quantitation of recombinantly produced fish growth hormone, an extinction coefficient of 700 $g^{-1}$ $cm^{-1}$ at 277 nm was assumed. This extinction coefficient is characteristic of bovine growth hormone (Burger et al., J. Biol. Chem. 241:449–457, 1966). The concentration of rPaGH and rEaGH was estimated by UV absorbance at 277 nm.

Circular dichroism (CD) spectra were determined on a Jasco J-720C spectropolarimeter. All spectra were determined at room temperature using a cuvette with 0. 1 cm path length. Data were expressed as the mean residue mole ellipticity (θ) (deg0$cm^2$/dmole), and were based on a molecular weight of 22 KD.

Cell proliferation assay. The ability of recombinant proteins to stimulate cell proliferation was examined using a MTS-formazan conversion assay (Promega). $10^4$ ZFL cells (Zebrafish liver cell line, described in Ghosh et al., Cell. Biol. Toxicol. 10:167–176, 1994) in log stage growth were seeded on 96-well plates. Various amounts of recombinant or control proteins were added into 100 μl culture medium (L15 [Gibco BRL] supplemented with 0.5% fetal bovine serum and 0.1% bovine serum albumin) to achieve a final concentration of recombinant growth hormone or control proteins ranging from 0.1 to 1×$10^6$ pM. The cells were then placed in contact with the recombinant proteins at 28° C. for 48 hours.

After the 48 hours incubation, 20 μl of CellTiter 96 Aqueous one solution (Promega) was added into each well, and the plates were incubated for 4 hours at 37° C. in a humidified, 5% $CO_2$ incubator. The absorbance of each well at 450 nm was recorded using a plate reader. CHO-K1 (Chinese hamster ovary) cells, which do not express a growth hormone receptor, was used as a control for effects independent from physiological binding of a growth hormone to its receptor on a cell. Transgenic fish. Fish growth hormone cDNA was inserted into a CMV expression vector as follows. The fish pituitary cDNA was synthesized using a ZAP-cDNA® synthesis kit (Stratagene, cat. no. 200400) and inserted into library vectors using the ZAP Express® vector XR kit (Stratagene, cat. no. 239213). The expression vector was then introduced into fish sperm cells using a Baekon 2000 electroporator. The settings for electroporation were 10 kV, 64 pulses, 4 cycles, 0.4 μs burst time, and 160 μs pulse time. Ten microliters of harvested fish seminal fluid containing sperm were mixed with 0.5 ml saline containing 100 ug/ml fish growth hormone cDNA expression vector. After electroporation, the sperm was mixed with mature fish eggs and saline for fertilization. The zygotes were incubated in 16 to 18° C. fresh water until hatching.

The gene transduction efficiency was evaluated by extracting genomic DNA from hatched fish and amplifying the transgene using primers hybridizing to the CMV promoter sequence and the introduced growth hormone sequence. The transgene was confirmed by the size and restriction enzyme digestion pattern of the amplified PCR fragment.

The results of this Example are described below. Degenerate primers for cloning fish growth hormones Using the growth hormone gene sequences of the common carp, tuna, red sea bream, rainbow trout, yellow tail, and chum salmon, a consensus growth hormone sequence was generated and used to design two primers. The sense primer was CAAMAYCTBCACCWRYTSGCYSMR (SEQ ID NO:13) and antisense primer was CTTGTGCATGT-CYTTYTTRAARCA (SEQ ID NO:14). The single letter codes for degenerate nucleotides are M=A or C; R=A or G; W=A or T; S=C or G; Y=C or T; K =G or T; V=A, C, or G; H=A, C, or T; D=A, G, or T; and B=C, G, or T. These primers were used to amplify a 456 bp, 450 bp, and 462 bp PCR product from ayu, yellow grouper, and zebrafish cDNA, respectively. These PCR fragments were used to synthesis DNA probes for cloning the complete full length growth hormone cDNA of ayu, yellow grouper, and zebrafish. Molecular cloning of growth hormone gene from ayu pituitary gland cDNA library A full length DNA clone of ayu growth hormone was isolated by screening an ayu pituitary cDNA library with ayu growth hormone DNA probes produced in Example 1. The nucleotide sequences of the ayu growth hormone cDNA clone was 1410 bp in length and encoded 208 amino acids (see SEQ ID NOs: 1 and 2 above). The 5' untranslated region was 68 bp in length, and the 3' untranslated region was 718 bp in length. A 22 amino acids signal peptide was predicted using the software program SignalP (Nielsen et al., Protein Eng. 10:1–6, 1997). Molecular cloning of growth hormone gene from a yellow grouper pituitary gland cDNA library A full length DNA clone of yellow grouper growth hormone was isolated by screening a yellow grouper pituitary cDNA library with the yellow grouper growth hormone DNA probes produced in Example 1. The nucleotide sequence of yellow grouper growth hormone cDNA clone was 972 bp in length, encoding 204 amino acid (see SEQ ID NOs:5 and 6). The 5' untranslated region was 69 bp in length and the 3' untranslated region was 291 bp in length. A 19 amino acid signal peptide was predicted using the software program SignalP (Nielsen et al., supra). Molecular cloning of zebrafish growth hormone gene A full length DNA clone of zebrafish growth hormone was isolated by screening a zebrafish head cDNA library using the zebrafish growth hormone probes produced in Example 1. The nucleotide sequence of the zebrafish growth hormone cDNA clone was 1195 bp in length, encoding 210 amino acids (see SEQ ID NOs:9 and 10). The 5' untranslated region was 37 bp in length, and the 3' untranslated region was 528 bp in length. A 22 amino acids signal peptide was predicted by the software program SignalP (Nielsen et al., supra) Expression of recombinant ayu growth hormone The DNA fragment encoding the mature ayu growth hormone was cloned into the PET-20b(+) expression vector (Novagen) to produce an open reading frame encoding the ayu growth hormone with an extra methionine at the amino terminus and extra Leu-Glu-His$_6$ (SEQ ID NO: 15) at the carboxyl terminus. The DNA fragment inserted into the expression vector was PCR-amplified using primers AATTCCATATGTCAGAGAACCAGCGTGTA (SEQ ID NO: 16) and CCGCTCGAGCAGGGTACAGTTGGCTTC (SEQ ID NO: 17).

The rPaGH was produce in transformed bacteria induced with IPTG. Cell lysates were divided into soluble and insoluble portions. Analysis of protein fractions by SDS-PAGE indicated that most of the recombinant protein was in the insoluble fraction. The molecular weight of rPaGH on SDS-PAGE was about 28 KD. The purity of rPaGH was about 74% of total insoluble protein, as determined by optical density. rPaGH was dissolvable in a reducing solvent containing 0.1 M β-mercaptoethanol, 4.5 M urea, and 5% glycerol (pH 12.4). The rPaGH was renatured by four-step equilibrium dialysis. The four steps were (1) dialysis for 48 hours in 10 mM Tris-HCl (pH 11), 1 M urea, 0.1 mM μ-mercaptoethanol, 1 mM cysteine, and 5% glycerol; (2) dialysis for 24 hours in 10 mM Tris-HCl (pH 11), 0.1 mM β-mercaptoethanol, 1 mM cysteine, and 5% glycerol; (3) dialysis for 12 hours in 10 mM Tris-HCl (pH 8.8), 5% glycerol, and 0.1 M β-mercaptoethanol; and (4) dialysis for 12 hours in 10 mM Tris-HCl (pH 8.8) and 0.1 M β-mercaptoethanol. Expression of recombinant yellow grouper growth hormone The DNA fragment encoding the mature yellow grouper growth hormone was cloned into the PET-20b(+) expression vector (Novagen) to produce an open reading frame encoding the yellow grouper growth hormone with an extra methionine at the amino terminus and extra Leu-Glu-His$_6$ (SEQ ID NO: 15) at the carboxyl terminus. The DNA fragment inserted into the expression vector was PCR-amplified using primers AATTCCATATGATCACAGACGGCCAGCGACTG (SEQ ID NO: 18) and CCGCTCGAGCAGGGTACGGTTGGCCTCAGG (SEQ ID NO:10).

The rEaGH was produce in transformed bacteria induced with IPTG. Cell lysates were divided into soluble and insoluble portions. Analysis of protein fractions by SDS-PAGE indicated that most of the recombinant protein was in the insoluble fraction. The molecular weight of rEaGH on SDS-PAGE was about 24 KD. The purity of rEaGH was about 90% of total insoluble protein, as determined by optical density. rEaGH was dissolvable in a reducing solvent containing 0.1 M β-mercaptoethanol, 4.5 M urea, and 5% glycerol (pH 12.6). The rEaGH was renatured by the four-step equilibrium dialysis procedure described in Example 5 above. Characterization of growth hormone folding CD spectra studies indicated that there were two broad negative absorption peaks at 218 nm and 211 nm and one positive absorption peak at 190 nm for both the refolded ayu and yellow grouper recombinant growth hormones. This is consistent with what is observed for native, purified human growth hormone. Similar spectra were observed for rEaGH, except that there were three negative absorption peaks at 254 nm, 263 nm, and 270 nm. Therefore, based on Yang's estimation (Yang et al., Methods Enzymol. 13:208–269, 1986), the secondary structure of folded rPaGH contained about 36% helix, 34% β-sheet, 5.1% β-turn, and 25.7% random coil, the RMS value being 8.36. It was also estimated that the secondary structure of folded rEaGH contained about 59% helix, 0% β-sheet, 24.6% βturn, and 16.5% random coil, the RMS value being 12.59. Bioactivity of recombinant growth hormones The bioactivity of recombinant growth hormones was evaluated using ZFL cells and a MTS-formazan conversion assay. A concentration of 1 βm, human growth hormone, rPaGH, and rEaGH increased cell proliferation, relative to no growth hormone added, by 13.7%, 118.3 %, and 58.3%, respectively. In addition, the increase in cell proliferation was dose dependent in the range from about 0.1 to $10^6$ pM. The proliferation of a CHO control cell line was not affected by the addition of any growth hormone, as expected, because these cells do not express a growth hormone receptor. Transgenic ayu overexpressing ayu growth hormone Ayu growth hormone cDNA was inserted into a CMV expression vector as described above. The expression vector was then introduced into ayu sperm cells, which were used to fertilize ayu fish eggs. After about 10 to 12 days, the fertilized eggs produced hatchlings. One hundred hatched ayu were sacrificed, and their genomic DNA was extracted. Eighty six of the hundred contained the CMV-ayu growth hormone expression cassette in their genomic DNA. The presence of the expression cassette was confirmed by the size of a DNA fragment amplified from the genomic DNA and by the BamHI I digestion pattern.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid encoding a polypeptide that comprises an amino acid sequence at least 75% identical to SEQ ID NO:2, at least 97% identical to SEQ ID NO:6, or at least 95% identical to SEQ ID NO:10, wherein said polypeptide is a fish growth hormone.

2. The isolated nucleic acid of claim 1, wherein the amino acid sequence is selected from the group consisting of SEQ ID NOs:2, 6, and 10.

* * * * *